United States Patent [19]

Kelly

[11] Patent Number: 4,954,655

[45] Date of Patent: Sep. 4, 1990

[54] PREPARATION OF ALKYLHYDRAZINES

[75] Inventor: Martha J. Kelly, Norristown, Pa.

[73] Assignee: Rohm and Haas Company, Philadelphia, Pa.

[21] Appl. No.: 331,925

[22] Filed: Mar. 31, 1989

[51] Int. Cl.$^5$ .................................. C07C 241/02
[52] U.S. Cl. ........................ 564/464; 564/313; 564/462
[58] Field of Search ............... 564/313, 464, 462

[56] References Cited

U.S. PATENT DOCUMENTS 4,310,696  1/1982  Hojo et al. ........................ 564/464
4,435,600  3/1984  Hasegawa et al. ................ 564/464

FOREIGN PATENT DOCUMENTS 63-72661  4/1988  Japan .

OTHER PUBLICATIONS

Derwent's Chemical Patents Index, Section C:AGDOC (Section JG, p. 4, week 8819), 6/22/88.
Chemical Abstracts 109: 148903m, vol. 109, No. 17, 10/24/88.
Solomons, *Organic Chemistry*, 2nd Ed., John Wiley and Sons, New York, (1980), pp. 220, 221, 240, and 241.
March, *Advanced Organic Chemistry, etc.*, 2nd Ed., McGraw-Hill, New York, (1977), pp. 694 and 695.

*Primary Examiner*—Glennon H. Hollrah
*Assistant Examiner*—Peter G. O'Sullivan
*Attorney, Agent, or Firm*—Barbara V. Maurer; Mervin E. Brokke

[57] ABSTRACT

This application relates to a process for preparing alkylhydrazines from an alkene and hydrazine with an acid catalyst. More particularly, it relates to a process for preparing t-butylhydrazine from hydrazine and isobutylene in aqueous acid.

15 Claims, No Drawings

PREPARATION OF ALKYLHYDRAZINES

This invention relates to a process for preparing alkylhydrazines. More particularly, this invention relates to a process which comprises reacting a substituted alkene with hydrazine in the presence of a strong acid to obtain a t-alkylhydrazine. The t-alkylhydrazines are useful intermediates in the process of preparing N-t-alkyl-1,2-diacylhydrazines which are known to have insecticidal activity against Coleoptera and Lepidoptera. The process of the present invention provides an ecomomic method of producing the desired t-alkylhydrazines from inexpensive and readily available starting materials.

Hasegawa et al., U.S. Pat. No. 4,435,600 discloses a process for the preparation of tertiary-butyl hydrazine by the direct reaction of t-butanol with a hydrazine salt of a hydrohalogenic acid in the precence of a hydrazine dihydrohalogenide or a hydrogen halide. The patent also discloses that the reaction of t-butanol with hydrazine hydrochloride in an autoclave resulted in the formation of isobutylene and that accordingly the hydrochloride of t-butylhydrazine was not formed.

In the process of the instant invention, the alkylhydrazines may be prepared by reacting a branched alkene with hydrazine in the presence of an acid catalyst.

The general reaction is shown in Equation I.

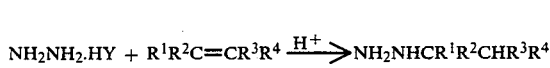

(I)

wherein $R^1$ is alkyl;

$R^2$ is alkyl, alkenyl, alkynyl or phenyl; $R^3$ is hydrogen, alkyl, alkenyl or alkynyl; or $R^1$ and $R^2$ together or $R^2$ and $R^3$ together respectively form a cycloalkyl group; and $R^4$ is hydrogen, alkyl, alkenyl or alkynyl. Hy is HOH, $H_2SO_4$ or hydrohalide.

Alkyl includes straight or branched alkyl groups for example $(C_1-C_4)$alkyl such as methyl, ethyl, propyl, butyl, isopropyl and the like. Alkenyl includes for example $(C_2-C_4)$alkenyl such as ethenyl, allyl, and the like. Alkynyl includes for example $(C_2-C_4)$alkynyl such as propargyl. Cycloalkyl includes for example $(C_5-C_8)$cycloalkyl such as cyclohexyl and the like. Examples of starting alkenes include isobutylene, 2-methyl-2-butene, 2,3-dimethyl-2-butene, 2-methyl-1-hexene, 1-methylcyclohexene, methylenecyclohexane, alpha-methyl styrene and the like. The term "halo" means chloro, fluoro, bromo and iodo.

The hydrazine used in the process can be a hydrazine hydrate or a hydrazine salt, for example hydrazine sulfate or a hydrazine hydrohalide, preferably a hydrohalide. The most preferred is hydrazine hydrochloride.

The acid catalysts include toluenesulfonic acid and other sulfonic acids, inorganic mineral acids, for example sulfuric acid, phosphoric acid($H_3PO_4$), or hydrohalogenic acid such as hydrochloric acid (HCl) hydrogen bromide or hydrogen iodide and acidic resins, for example Amberlyst ® 15(wet) ion-exchange resin, Amberlyst ® XN100 ion-exchange resin and the like, and combinations thereof. An acidic clay, such as Montmorillonite can also be used.

The reaction process is preferably carried out in the presence of a polar solvent such as water, a low molecular weight alcohol, for example methanol, ethanol, propanol and the like or mixtures thereof. Low molecular weight alcohols include those alcohols which are liquids at the reaction temperature. The preferred solvents are water, methanol, ethanol, propanol, and mixtures thereof.

The reaction process is carried out at atmospheric pressure or under pressure.

Depending on the reactants, catalyst and solvent, the process is carried out between about $-20°$ C. and about $150°$ C. Preferably, the process is carried out between about $0°$ C. and about $120°$ C. The preferred range is about $50°$ C. to about $100°$ C.

The following examples further illustrate the invention but are not intended to limit it in any way.

EXAMPLE No. 1

Hydrazine hydrochloride (11.81 grams(g), 0.160 mole), water (60 g) and hydrochloric acid (19.50 g, 37.5%) were combined and heated to 95° C. under nitrogen. Excess isobutylene(600 g) was bubbled through the reaction mixture for 11 hours.

The reaction mixture was transferred to a 500 milliliter (mL) flask with an additional 20 mL of water, and cooled. Sodium hydroxide solution (50%, 29.6 g, 0.3 mole) was added, keeping the temperature below 10° C. This was followed by the addition to 90 mL of methylene chloride. A solution of benzoyl chloride (47.71 g, 0.336 mole) in 20 mL of methylene chloride and a solution of sodium hydroxide (27.2 g, 50%, 0.34 mole) in approximately 30 mL of water were added dropwise, simultaneously, over 45 minutes, keeping the temperature at 15°-20° C. The reaction mixture was allowed to warm to room temperature, where it was maintained for 2 hours. The phases were separated, and the organic phase was stripped to yield 46.39 g of white solids. This material was analyzed by HPLC against weighed standards as being 81% 1-t-butyl-1,2-dibenzoylhydrazide (79% yield calculated from the starting hydrazine).

EXAMPLE No. 2

To a solution of hydrazine hydrochloride (11.18 g, 98% purity, 0.160 mole) in 60 g of water was added 19.50 g of 37% hydrochloric acid solution. The solution was heated to 90° C. 2,3-Dimethyl-2-butene (13.74 g, 98% purity, 0.160 mole) was added over 4 hours by syringe pump. The addition of the olefin caused the internal temperature of the reaction mixture to drop to 71° C. After the addition was complete, the reaction mixture was held for 6 hours at 75°-82° C. A sample of the solution was taken and reacted with benzoyl chloride and sodium hydroxide as described in Example 1 to convert all the hydrazines present to their dibenzoyl derivatives. Analysis by GC indicated a 25% conversion to the expected 1,1,2-trimethylpropylhydrazine.

EXAMPLE No. 3

The procedure of Example 1 was carried out using 15 mL of water, 25 mL propanol, 36.2 g aqueous HCl (37.5%) and 6.85 g hydrazine hydrochloride to yield 59% of the expected product.

The following examples of the invention are prepared according to the procedure of Example 1 by substituting the appropriate reagents as listed in Table 1.

TABLE I

| Example No. | Hydrazine | Acid | Solvent | Olefin |
|---|---|---|---|---|
| 4 | hydrazine | sulfuric | water | isobutylene |

TABLE I-continued

| Example No. | Hydrazine | Acid | Solvent | Olefin |
|---|---|---|---|---|
| 5 | sulfate hydrazine hydrochloride | acid anhydrous hydrogen chloride | methanol | isobutylene |

The following examples of the invention are prepared according to the procedure of Example 2 by substituting the appropriate reagents as indicated in Table II.

TABLE II

| Example No | Hydrazine | Acid | Solvent | Olefin |
|---|---|---|---|---|
| 6 | hydrazine hydrochloride | hydrochloric acid | water | 2-methyl-1-hexene |
| 7 | hydrazine hydrochloride | hydrochloric acid | water | 1-methyl-cyclo-hexene |
| 8 | hydrazine sulfate | sulfuric acid | water | alpha-methyl-styrene |
| 9 | hydrazine hydrochloride | hydrochloric acid | water | 2-methyl-1,4-penta-diene |
| 10 | hydrazine hydrochloride | hydrochloric acid | water | 4-methyl-1,3-penta-diene |
| 11 | hydrazine hydrochloride | hydrochloric acid | water | methyl-enecylo-hexane |

EXAMPLE No. 11

Hydrazine hydrochloride (0.69 g, 0.01 mole), water (3.75 g), hydrochloric acid (1.2 g, 37.5%) and isobutylene (0.9 g, 0.016 mole) were charged into an autoclave at 35 psig and heated to 85° C. for 12 hours to yield t-butylhydrazine hydrochloride.

It should be understood that the instant specification and examples are set forth by way of illustration and not limitation, and what various modifications and changes may be made without departing from the spirit and scope of the present invention as defined by the appended claims.

I claim:

1. A process for preparing an alkylhydrazine of the formula $H[N]_2NNHCR^1R^2CHR^3R^4$ which comprises reacting hydrazine and an alkene of the formula $R^1R^2C=CR^3R^4$ wherein
$R^1$ is $(C_1-C_4)$ alkyl;
$R^2$ is $(C_1-C_4)$ alkyl, $(C_2-C_4)$ alkenyl, $(C_2-C_4)$ alkynyl or phenyl;
$R^3$ is hydrogen, $(C_1-C_4)$ alkyl, $(C_2-C_4)$ alkenyl or $(C_2-C_4)$ alkynyl; or $R^1$ and $R^2$ together or $R^2$ and $R^3$ together respectively form a cycloalkyl group; and
$R^4$ is hydrogen, $(C_1-C_4)$ alkyl, $(C_2-C_4)$ alkenyl or $(C_2-C_4)$ alkynyl; in the presence of an acid catalyst.

2. The process of claim 1 wherein the process is carried out at atmospheric pressure.

3. The process of claim 1 which is carried out under pressure.

4. The process of claim 1 wherein the alkene is selected from the group consisting of isobutylene, 2-methyl-2-butene, 2,3-dimethyl-2-butene, 2-methyl-1-hexene, 1-methylcyclohexene, methylenecyclohexane and alpha-methyl styrene.

5. The process of claim 1 wherein the acid is selected from the group consisting of hydrogen bromide, hydrogen chloride, hydrogen iodide, toluenesulfonic acid, sulfuric acid, phosphoric acid, acidic ion-exchange resin, or an acidic clay or a mixture thereof.

6. The process of claim 5 wherein the acid is hydrogen chloride or sulfuric acid.

7. The process of claim 1 which is carried out at a temperature between about −50° C. and about 150° C.

8. The process of claim 7 which is carried out at a temperature between about 0° C. about 120° C.

9. The process of claim 8 which is carried out at a temperature between about 50° C. and about 100° C.

10. The process of claim 1 which is carried out in water or $(C_1-C_6)$ aliphatic alcohol.

11. The process of claim 9 which is carried out in water, methanol, ethanol, or propanol.

12. The process of claim 1 which is carried out using hydrazine hydrochloride and hydrogen chloride in water.

13. The process of claim 11 wherein the alkene is isobutylene or 2,3-dimethyl-2-butene.

14. The process of claim 12 which is carried out between about 50° and about 100° C.

15. The process of claim 13 wherein the alkene is isobutylene.

* * * * *